(12) United States Patent
Ralph et al.

(10) Patent No.: US 6,645,249 B2
(45) Date of Patent: Nov. 11, 2003

(54) INTERVERTEBRAL SPACER DEVICE HAVING A MULTI-PRONGED DOMED SPRING

(75) Inventors: James D. Ralph, Seaside Park, NJ (US); Stephen Tatar, Montvale, NJ (US); Joseph P. Errico, Kirkland, WA (US)

(73) Assignee: SpineCore, Inc., Summit, NJ (US)

( * ) Notice: Subject to any disclaimer, the term of this patent is extended or adjusted under 35 U.S.C. 154(b) by 117 days.

(21) Appl. No.: 10/035,668

(22) Filed: Nov. 9, 2001

(65) Prior Publication Data

US 2003/0078665 A1 Apr. 24, 2003

Related U.S. Application Data

(63) Continuation-in-part of application No. 09/982,148, filed on Oct. 18, 2001.

(51) Int. Cl.[7] .................................................. A61F 2/44
(52) U.S. Cl. .............................. 623/17.13; 623/17.14; 623/17.15
(58) Field of Search ......................... ; 623/17.13–17.15, 623/17.16; A61F 2/44

(56) References Cited

U.S. PATENT DOCUMENTS

| | | | |
|---|---|---|---|
| 5,458,642 A | 10/1995 | Beer et al. | |
| 5,556,431 A | 9/1996 | Buttner-Janz | |
| 5,562,738 A | 10/1996 | Boyd et al. | |
| 5,674,296 A | 10/1997 | Bryan et al. | |
| 5,676,701 A | 10/1997 | Yuan et al. | |
| 5,676,702 A | 10/1997 | Ratron | |
| 5,683,465 A | 11/1997 | Shinn et al. | |
| 5,755,796 A | 5/1998 | Ibo et al. | |
| 5,827,328 A | 10/1998 | Buttermann | |
| 5,865,846 A | 2/1999 | Bryan et al. | |
| 5,888,226 A | 3/1999 | Rogozinski | |
| 5,895,428 A | 4/1999 | Berry | |
| 5,899,941 A | 5/1999 | Nishijima | |
| 5,989,291 A | 11/1999 | Ralph et al. | |
| 6,001,130 A | 12/1999 | Bryan et al. | |
| 6,019,792 A | 2/2000 | Cauthen | |
| 6,039,763 A | 3/2000 | Shelokov | |
| 6,063,121 A | 5/2000 | Xavier et al. | |
| 6,113,637 A | 9/2000 | Gill et al. | |
| 6,136,031 A | 10/2000 | Middleton | |
| 6,146,421 A | 11/2000 | Gordon et al. | |
| 6,156,067 A | 12/2000 | Bryan et al. | |
| 6,179,874 B1 | 1/2001 | Cauthen | |
| 6,228,118 B1 | 5/2001 | Gordon | |
| 6,368,350 B1 * | 4/2002 | Erickson et al. | 623/17.14 |
| 6,572,653 B1 * | 6/2003 | Simonson | 623/17.13 |
| 2002/0035400 A1 * | 3/2002 | Bryan et al. | 623/17.15 |
| 2003/0083749 A1 * | 5/2003 | Kuslich et al. | 623/17.16 |

FOREIGN PATENT DOCUMENTS

| | | | | |
|---|---|---|---|---|
| FR | 2 718 635 A1 * | 10/1995 | | A61F/2/44 |
| FR | 2 730 159 A1 * | 8/1996 | | A61F/2/44 |
| FR | 2 805 985 A1 * | 9/2001 | | A61F/2/44 |
| WO | WO 01/01893 A1 * | 1/2001 | | A61F/2/44 |
| WO | WO 01/93785 A2 * | 12/2001 | | A61F/2/44 |

* cited by examiner

*Primary Examiner*—David H. Willse
*Assistant Examiner*—Javier G. Blanco
(74) *Attorney, Agent, or Firm*—Joseph P. Errico, Esq.; Timothy J. Bortree, Esq.

(57) ABSTRACT

An intervertebral spacer device having a pair of opposing plates for seating against opposing vertebral bone surfaces, separated by a spring mechanism. The preferred spring mechanism is a multi-pronged domed spring which is coupled to the upper plate by set screws. The spring includes a socket formed in the peak thereof and mounts onto a ball-shaped head extending outwardly from the lower plate. The spring and post members are thereby flexibly coupled such that the upper and lower plates may rotate relative to one another.

6 Claims, 3 Drawing Sheets

INTERVERTEBRAL SPACER DEVICE HAVING A MULTI-PRONGED DOMED SPRING

CROSS-REFERENCE TO RELATED APPLICATION

This application is a continuation in part of U.S. patent application Ser. No. 09/982,148 filed Oct. 18, 2001 and entitled "An Intervertebral Spacer Device Having Arch Shaped Spring Elements", which is fully incorporated herein by reference.

FIELD OF THE INVENTION

This invention relates generally to a spinal implant assembly for implantation into the intervertebral space between adjacent vertebral bones to simultaneously provide stabilization and continued flexibility and proper anatomical motion.

BACKGROUND OF THE INVENTION

The bones and connective tissue of an adult human spinal column consists of more than 20 discrete bones coupled sequentially to one another by a tri-joint complex which consists of an anterior disc and the two posterior facet joints, the anterior discs of adjacent bones being cushioned by cartilage spacers referred to as intervertebral discs. These more than 20 bones are anatomically categorized as being members of one of four classifications: cervical, thoracic, lumbar, or sacral. The cervical portion of the spine, which comprises the top of the spine, up to the base of the skull, includes the first 7 vertebrae. The intermediate 12 bones are the thoracic vertebrae, and connect to the lower spine comprising the 5 lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

The spinal column of bones is highly complex in that it includes over twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes which can result in spinal pathologies for which surgical intervention may be necessary. A variety of systems have been disclosed in the art which achieve immobilization and/or fusion of adjacent bones by implanting artificial assemblies in or on the spinal column. The region of the back which needs to be immobilized, as well as the individual variations in anatomy, determine the appropriate surgical protocol and implantation assembly. With respect to the failure of the intervertebral disc, the interbody fusion cage has generated substantial interest because it can be implanted laparoscopically into the anterior of the spine, thus reducing operating room time, patient recovery time, and scarification.

Referring now to FIGS. 1 and 2, in which a side perspective view of an intervertebral body cage and an anterior perspective view of a post implantation spinal column are shown, respectively, a more complete description of these devices of the prior art is herein provided. These cages 10 generally comprise tubular metal body 12 having an external surface threading 14. They are inserted transverse to the axis of the spine 16, into preformed cylindrical holes at the junction of adjacent vertebral bodies (in FIG. 2 the pair of cages 10 are inserted between the fifth lumbar vertebra (L5) and the top of the sacrum (S1). Two cages 10 are generally inserted side by side with the external threading 14 tapping into the lower surface of the vertebral bone above (L5), and the upper surface of the vertebral bone (S1) below. The cages 10 include holes 18 through which the adjacent bones are to grow. Additional material, for example autogenous bone graft materials, may be inserted into the hollow interior 20 of the cage 10 to incite or accelerate the growth of the bone into the cage. End caps (not shown) are often utilized to hold the bone graft material within the cage 10.

These cages of the prior art have enjoyed medical success in promoting fusion and grossly approximating proper disc height. It is, however, important to note that the fusion of the adjacent bones is an incomplete solution to the underlying pathology as it does not cure the ailment, but rather simply masks the pathology under a stabilizing bridge of bone. This bone fusion limits the overall flexibility of the spinal column and artificially constrains the normal motion of the patient. This constraint can cause collateral injury to the patient's spine as additional stresses of motion, normally borne by the now-fused joint, are transferred onto the nearby facet joints and intervertebral discs. It would therefore, be a considerable advance in the art to provide an implant assembly which does not promote fusion, but, rather, which nearly completely mimics the biomechanical action of the natural disc cartilage, thereby permitting continued normal motion and stress distribution.

It is, therefore, an object of the present invention to provide a new and novel intervertebral spacer which stabilizes the spine without promoting a bone fusion across the intervertebral space.

It is further an object of the present invention to provide an implant device which stabilizes the spine while still permitting normal motion.

It is further an object of the present invention to provide a device for implantation into the intervertebral space which does not promote the abnormal distribution of biomechanical stresses on the patient's spine.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a flexible intervertebral spacer device comprising a pair of spaced apart base plates, arranged in a substantially parallel planar alignment (or slightly offset relative to one another in accordance with proper lordotic angulation) and coupled to one another by means of at least one spring mechanism. This at least one spring mechanism provides a strong restoring force when a compressive load is applied to the plates, and may also permit limited rotation of the two plates relative to one another. While there are a wide variety of embodiments contemplated, one preferred embodiment is described herein as representative of preferred types.

More particularly, with respect to the base plates, which are largely similar in all embodiments, as the assembly is to be positioned between the facing surfaces of adjacent vertebral bodies, and as such need to have substantially flat external surfaces which seat against the opposing bone surfaces. Inasmuch as these bone surfaces are often concave, it is anticipated that the opposing plates may be convex in accordance with the average topology of the spinal anatomy. In addition, the plates are to mate with the bone surfaces in such a way as to not rotate relative thereto. (The plates rotate relative to one another, but not with respect to the bone surfaces to which they are each in contact with.) In order to prevent rotation of a plate relative to the bone, the upper and lower plates alternatively may each include outwardly directed spikes which penetrate the bone surface and mechanically hold the plates in place. However, it is more preferably anticipated that the plates should include a porous coating into which the bone of the vertebral body can grow. The most desirable upper and lower plate surface porous feature is a deflectable wire mesh into which the bone can readily grow, and which mesh will deform to seat into the concave upper and lower bone faces. (Note that this limited fusion of the bone to the base plate does not extend across the intervertebral space.) These features, while being preferred are not required.

Between the base plates, on the exterior of the device, there may also be included a circumferential wall which is resilient and which simply prevents vessels and tissues from entering within the interior of the device. This resilient wall may comprise a porous fabric or a semi-impermeable elastomeric material. Suitable tissue compatible materials meeting the simple mechanical requirements of flexibility and durability are prevalent in a number of medical fields including cardiovascular medicine, wherein such materials are utilized for venous and arterial wall repair, or for use with artificial valve replacements. Alternatively, suitable plastic materials are utilized in the surgical repair of gross damage to muscles and organs. Still further materials which could be utilized herein may be found in the field of orthopedic in conjunction with ligament and tendon repair. It is anticipated that future developments in this area will produce materials which are compatible for use with this invention, the breadth of which shall not be limited by the choice of such a material. For the purposes of this description, however, it shall be understood that such a circumferential wall is unnecessary, and in some instances may be a hindrance, and thusly is not included in the specific embodiment set forth hereinbelow.

As introduced above, the internal structure of the present invention comprises a spring member, or other equivalent subassembly which provides a restoring force when compressed. It is desirable that the restoring forces be directed outward against the opposing plates, when a compressive load is applied to the plates. More particularly, the restoring force providing subassembly comprises a multi-pronged domed metal arch spring which is secured to the lower plate and against movement therefrom at its lateral ends. The domed spring comprises a plurality of flat ends (three to five in the preferred embodiments) disposed at the distal ends of the multi-prongs and a curvate or domed central portion. The curvate central portion is comprises a dome, or a shell. Stated alternatively, entire spring mechanism comprises a domed piece of metal which has curvate sections removed from the circumferential edge such that the element comprised a contiguous central curvate portion and a plurality (equal to the number of curvate sections removed) of curvate prongs which extend outward and downward. The flat lateral pieces which extend out from these prongs are the portions which are secured to the upper plate.

The domed portions of the strips deflect under loading, but provide a restoring force in opposition to the loading until they are permitted to regain their original shape. The restoring force of the spring is proportional to the elastic properties of the material as well as the length and arc of the curvate central portion of the strip (and the length and width of the prongs). The elasticity of the metal, which endures and counteracts the strain of the material, causes a deflection in the height of the arch.

In the preferred embodiment, the peak of the domed arch (central portion) further comprises a socket for flexibly coupling to a post member on the interior surface of the opposing plate. This post couples to the spring to form a ball and socket joint at the peak of the domed arch, which joint permits the plates to rotate relative to one another. This rotation may be constrained by the specific conformation of the joint such that the plates are free to rotate through only a range of angles.

More particularly, this embodiment comprises a pair of spaced apart base plates, one of which includes means for coupling the flat lateral ends of the domed spring thereto it (such as simple set screws). The other of the plates is similarly shaped, having a flat exterior surface (which may include a mesh or porous coating to permit bony ingrowth), but further includes a short central post portion which rises out of the interior face at a nearly perpendicular angle. The top of this short post portion includes a ball-shaped knob. The knob includes a central threaded axial bore which receives a small set screw. Prior to the insertion of the set screw, the ball-shaped head of the post can deflect radially inward (so that the ball-shaped knob contracts). The insertion of the set screw eliminates the capacity for this deflection.

As introduced above, a domed arch spring is mounted to this ball-shaped knob in such a way that it may rotate freely through a range of angles equivalent to the fraction of normal human spine rotation (to mimic normal disc rotation). In order to couple with the post, the strip spring includes an socket which accommodates the ball-shaped portion of the post. More particularly, the socket includes a curvate volume having a substantially constant radius of curvature which is also substantially equivalent to the radius of the ball-shaped head of the post. The deflectability of the ball-shaped head of the post, prior to the insertion of the set screw, permits the head to be inserted into the interior volume at the center of the spring, and the washer to be rotated into the proper lordotic angulation. Subsequent introduction of the set screw into the axial bore of the post flexibly retains the head in the socket of the spring. This assembly provides ample spring-like performance with respect to axial compressive loads, as well as long cycle life to mimic the axial biomechanical performance of the normal human intervertebral disc.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

Figure 1:
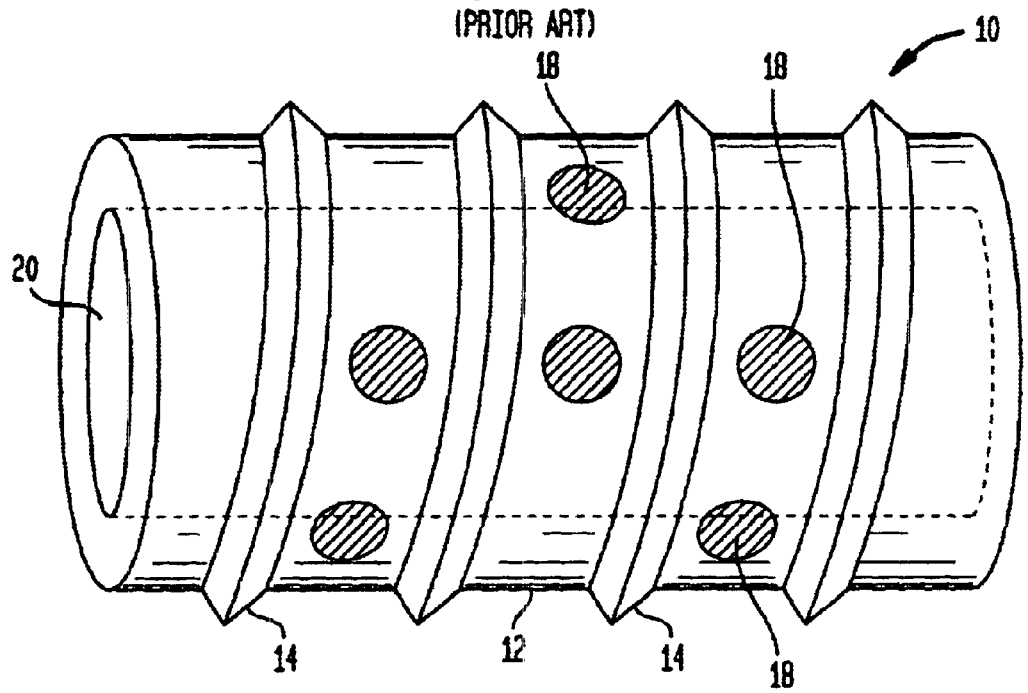
FIG. 1 is a side perspective view of an interbody fusion device of the prior art.
Figure 2:
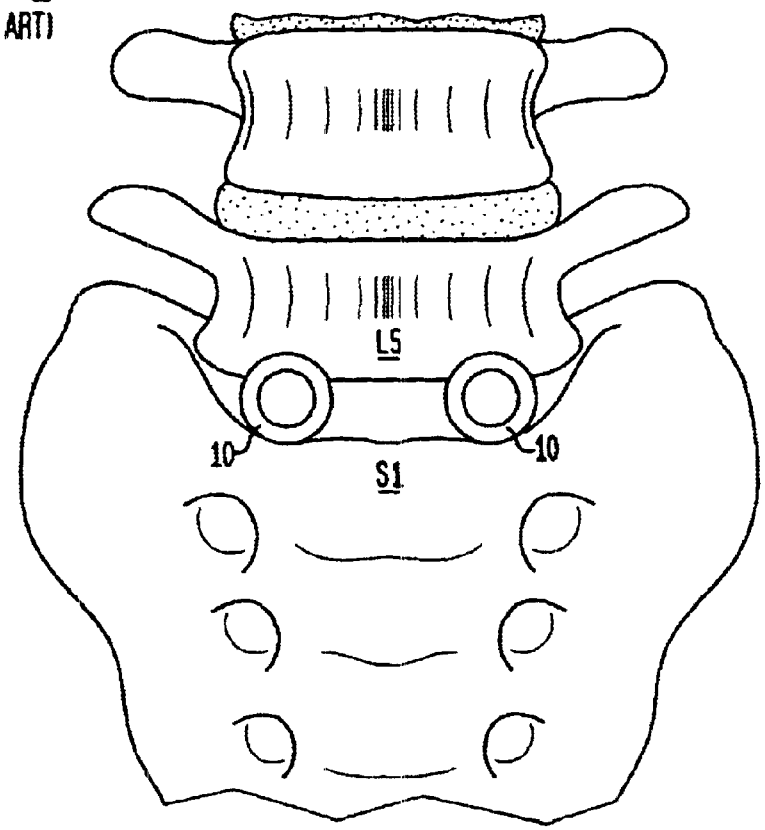
FIG. 2 is a front view of the anterior portion of the lumbo-sacral region of a human spine, into which a pair of interbody fusion devices of the type shown in FIG. 1 have been implanted.
Figure 3A:
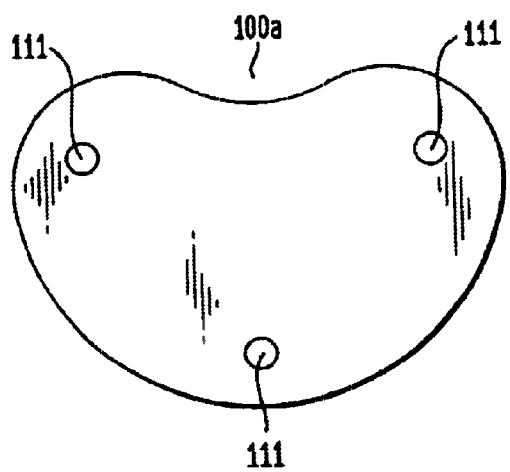
FIGS. 3a and 3b are top views of the upper and lower opposing plates of one embodiment of the present invention.
Figure 3B:
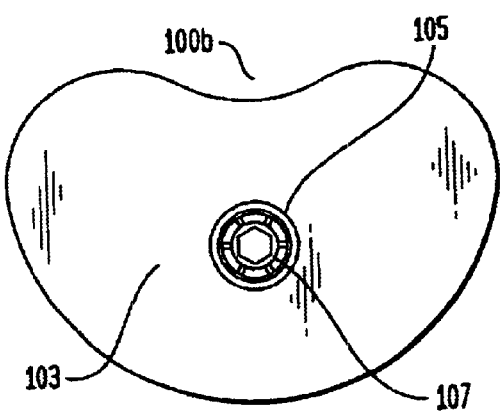

Referring now to FIGS. 3a and 3b, side cross-section views of the top and bottom plate members 100a 100b of a first embodiment of the present invention are shown. More particularly, in this embodiment, the upper and lower plates 100a,100b are nearly identical. As the device is designed to be positioned between the facing surfaces of adjacent vertebral bodies, the plates include substantially flat surface portions 102a,102b which seat against the opposing bone surfaces. In addition, the plates are to mate with the bone surfaces in such a way as to not rotate relative thereto. It is, therefore, preferred that the plates should include a porous coating into which the bone of the vertebral body can grow. The most desirable upper and lower plate surface porous feature is a deflectable wire mesh into which the bone can readily grow, and which mesh 104a,104b (see FIGS. 4b and 5) will deform to seat into the concave upper and lower bone faces. (Note that this limited fusion of the bone to the base plate does not extend across the intervertebral space.)

Plate 100a further includes a single set of threaded holes 111 for receiving the set screws (shown in FIG. 4b) required to affix the lateral ends of the multi-pronged domed arch strip spring thereto it.

Figure 4A:
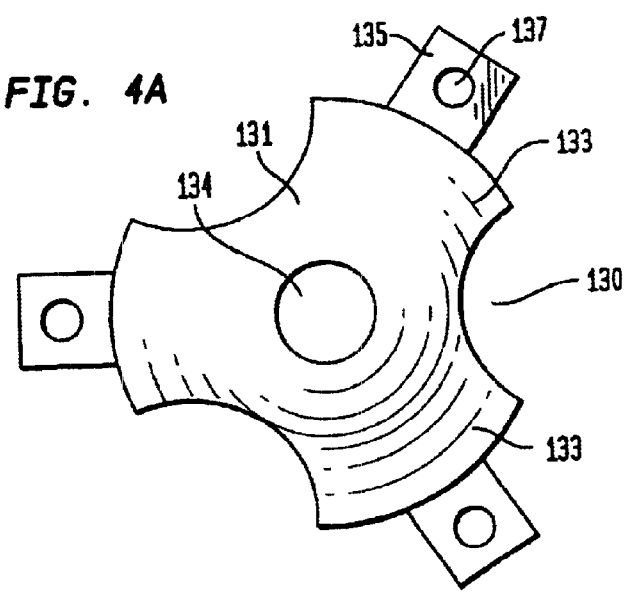
FIGS. 4a and 4b are a top view and side cross section view of a domed spring and a domed spring mounted to a lower plate.
Figure 4B:
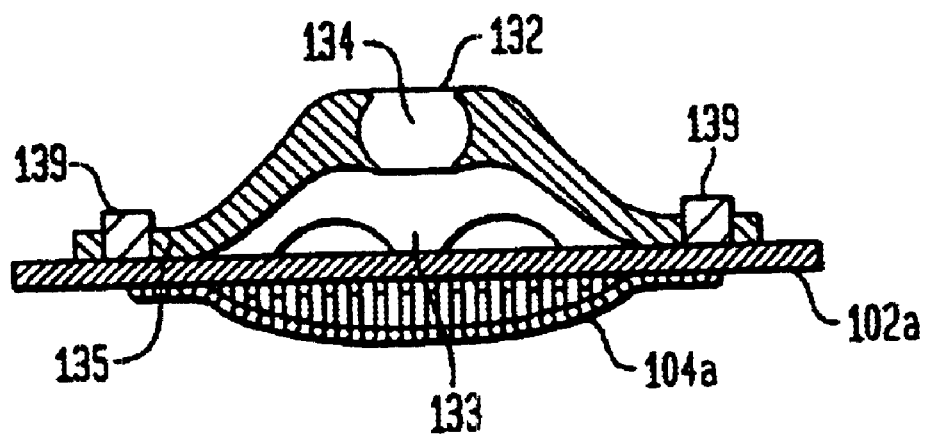
Figure 5:
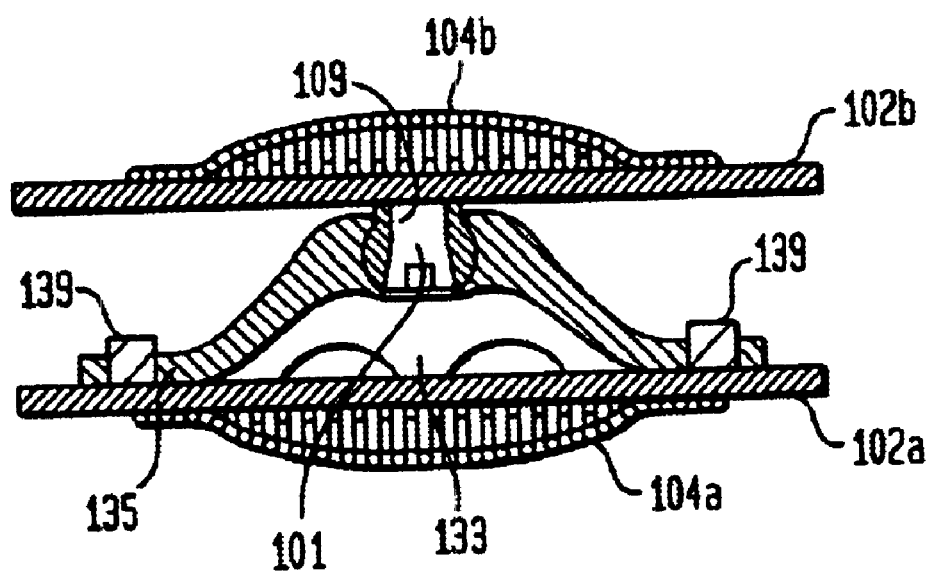
FIG. 5 is a side cross-section view of a second embodiment of the present invention which utilizes the elements shown in FIGS. 3a, 3b, 4a, and 4b.

Referring also to FIGS. 4b and 5, plate 100b has a similar shaped to the plates described above, i.e., having a flat exterior surface 102b which is designed to seat against the exposed opposing bone face in an intervertebral space, but plate 100b further includes a short central post member 105 which rises out of the interior face 103 at a nearly perpendicular angle. The top of this short post member 105 includes a ball-shaped head 107. The head 107 includes a central threaded axial bore 109 which extends down the post 105. This threaded bore 109 is designed to receive a small set screw 101. Prior to the insertion of the set screw 101, the ball-shaped head 107 of the post 105 can deflect radially inward (so that the ball-shaped head contracts). The insertion of the set screw 101 eliminates the capacity for this deflection.

Referring now to FIG. 4a, the multi-pronged domed arch spring 130 of this embodiment is shown in a top view. The spring 130 comprises a central domed portion 131 which includes a central socket portion (more fully described hereinbelow with respect to FIG. 4b), a plurality of curvate prongs 133 which extend outwardly and downwardly from the outer edges of the central domed portion, and a corresponding plurality of laterally extending tabs 135 joined at the lateral ends of the prongs 133. More particularly, the entire domed portion of the spring 130 is formed of a single contiguous shell member which has had several curvate portions removed from the lateral edge thereof. These removed portions are spaced about the circumference of the spring, leaving a series of prong shaped extending members 133 extending downward and outward along the arc of the shell. The lateral tabs 135 extend outwardly from the ends of the prongs 133 and have holes 137 therethrough for being attached to the upper plate 100a, with set screws 139.

Referring now to FIG. 4b, this multi-pronged domed spring 130 further includes the additional feature of having an enlarged central opening 132. This central opening 132 includes a curvate volume 134 for receiving therein the ball-shaped head 107 of the post 105 of the lower plate 100b described above. More particularly, the curvate volume 134 has a substantially constant radius of curvature which is also substantially equivalent to the radius of the ball-shaped head 107 of the post 105.

Referring also to FIG. 5, in which the fully assembled second embodiment of the present invention is shown, the combination and assembly of this embodiment is now provided. The deflectability of the ball-shaped head 107 of the post 105, prior to the insertion of the set screw 101, permits the head 107 to be inserted into the interior volume 134 at the peak of the domed arch strip spring 130. Subsequent introduction of the set screw 101 into the axial bore 109 of the post 101 flexibly couples the head 107 to the spring 130 by virtue of the head 107 not being compressible and removable from the central volume 134, but the post 105 being polyaxially retained in the socket 134. Ideally the post head 107 is locked loosely enough within the central volume 134 of the spring 130 such that anatomically relevant rotation of the plates 100a,100b remains viable. In alternative variation, however, it is possible to design the coupling such that the locking of the set screw 101 in the head 107 locks the assembly in one rotational orientation, preventing free rotation of the plates relative to one another. A combined embodiment may be one in which the set screw 101 may be selectively positioned in an unlocked (but still securing for the purpose of retention) and a locked orientation.

While there has been described and illustrated embodiments of an intervertebral spacer device, it will be apparent to those skilled in the art that variations and modifications are possible without deviating from the broad spirit and principle of the present invention. The present invention shall, therefore, not be limited solely to the specific embodiments disclosed herein.

We claim:

1. An intervertebral spacer device, comprising:
   first and second plate members, each having plate surfaces thereof, said plates being disposed in a spaced apart relationship such that inner ones of said plate surfaces oppose one another, and external ones of said plate surfaces face in opposite directions;
   and at least one multi-pronged domed spring restoring force providing element disposed between the inner surfaces of said first and second plate members, and disposed such that a compressive load applied to the external faces of said plates is counteracted by said at least one restoring force providing element,
   wherein said second plate further comprises a post structure rising off the inner surface thereof, and which post structure includes a ball-shaped head.

2. The device as Bet forth in claim 1, wherein at least one of said external surfaces of said first and second plates comprises a porous coating.

3. The device as set forth in claim 1, wherein said post structure further includes a threaded bore which extends axially from said ball-shaped head downwardly, and which bore receives therein a threaded set screw such that prior to insertion of the set screw therein, said bore permits the ball-shaped head to compress radially inwardly, and such that after the insertion of said set screw said ball-shaped head is not readily radially compressible.

4. The device as set forth in claim 3, wherein said at least one multi-pronged domed spring further comprises a central opening which includes a curvate volume for receiving and holding therein said ball-shaped head.

5. An intervertebral spacer device, comprising first and second plate members, each having plate surfaces thereof, said plates being disposed in a spaced apart relationship such that inner ones of said plate surfaces oppose one another, and external ones of said plate surfaces face in opposite directions;

said second plate member further including a post structure using off the inner surface thereof, and which post structure includes ball shaped head; and a multi-pronged domed spring, having a central peak portion, said peak portion including a central opening which includes a curvate volume for receiving and holding therein said ball-shaped head, such that a compressive load applied to the external faces of said plates is counteracted by a restoring force of said spring.

6. The device as set forth in claim 5, wherein said post structure further comprises a threaded bore which extends axially from said ball-shaped head downwardly, and which bore receives therein a threaded set screw such that prior to insertion of the set screw therein, said bore permits the ball-shaped head to compress radially inwardly, and such that after the insertion of said set screw said ball-shaped head is not readily radially compressible.

* * * * *

UNITED STATES PATENT AND TRADEMARK OFFICE
CERTIFICATE OF CORRECTION

PATENT NO. : 6,645,249 B2
DATED : November 11, 2003
INVENTOR(S) : James D. Ralph, Stephen Tatar and Joseph P. Errico It is certified that error appears in the above-identified patent and that said Letters Patent is hereby corrected as shown below:

Column 6,
Line 59, "," should read -- ; --;
Line 63, "Bet" should read -- set --.

Column 7,
Line 18, "using" should read -- rising --.
Line 19, after "includes" insert -- a --.

Signed and Sealed this

Eleventh Day of January, 2005

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,645,249 B2 | Page 1 of 1 |
| APPLICATION NO. | : 10/035668 | |
| DATED | : November 11, 2003 | |
| INVENTOR(S) | : James D. Ralph, Stephen Tatar and Joseph P. Errico | |

It is certified that error appears in the above-identified patent and that said Letters Patent is hereby corrected as shown below:

On the face of the patent, the residence for Stephen Tatar, should read --Montville, NJ--, not "Montvale, NJ"

Signed and Sealed this

Twenty-fourth Day of October, 2006

JON W. DUDAS
*Director of the United States Patent and Trademark Office*